United States Patent
Kollias et al.

(10) Patent No.: US 6,689,094 B2
(45) Date of Patent: Feb. 10, 2004

(54) COMPOUND DELIVERY USING IMPULSE TRANSIENTS

(75) Inventors: Nikiforos Kollias, Watertown, MA (US); Apostolos G. Doukas, Belmont, MA (US); Thomas J. Flotte, Boston, MA (US); Daniel J. McAuliffe, Boxford, MA (US); Shun Lee, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 36 days.

(21) Appl. No.: 09/891,096

(22) Filed: Jun. 25, 2001

(65) Prior Publication Data

US 2002/0062101 A1 May 23, 2002

Related U.S. Application Data

(63) Continuation of application No. 08/978,954, filed on Nov. 26, 1997, now Pat. No. 6,251,099.
(60) Provisional application No. 60/031,882, filed on Nov. 27, 1996.

(51) Int. Cl.[7] .............................................. A61M 31/00
(52) U.S. Cl. ....................................................... 604/69
(58) Field of Search ........................ 604/70, 69, 20–21, 604/500; 606/2.5

(56) References Cited

U.S. PATENT DOCUMENTS

| | | | |
|---|---|---|---|
| 4,775,361 A | 10/1988 | Jacques et al. ................ 604/20 |
| 5,041,121 A | * 8/1991 | Wondrazek et al. | |
| 5,152,768 A | * 10/1992 | Bhatta | |
| 5,386,837 A | 2/1995 | Sterzer ....................... 128/898 |
| 5,421,816 A | 6/1995 | Lipkovker ................... 604/20 |
| 5,614,502 A | 3/1997 | Flotte et al. .................. 514/34 |
| 5,656,016 A | 8/1997 | Ogden .......................... 601/2 |
| 5,713,845 A | 2/1998 | Tankovich ................... 604/20 |

OTHER PUBLICATIONS

Oosterhof et al., "Effects of High–Energy Shock Waves Combined With Biological Response Modifiers in Different Human Kidney Cancer Xenografts", *Ultrasound in Medicine and Biology*, 17:391–399, 1991.

Payne et al., "Sound Skin Models—Acoustic Properties of Epidermis and Dermis", *Skin Models To Study Function and Disease of Skin*, Parks et al., ed., Springer Verlag, Berlin, pp. 402–411, 1986.

Russo et al., "High Energy Shock Waves Suppress Tumor Growth In Vitro and In Vivo", *The Journal of Urology*, 135:626–628, 1986.

Singh et al., "Transdermal Drug Delivery by Passive Diffusion and Iontophoresis: A Review", *Medicinal Research Reviews*, 13:569, 1993.

Skauen et al., "Phonophoresis", *International Journal of Pharmaceutics*, 20:235–245, 1984.

Ter Haar, "Biological Effects of Ultrasound in Clinical Applications", In Ultrasound: Its Chemical, Physical, and Biological effects, Suslick, ed., VCH Publishers, pp. 305–320; 1988.

Umemura et al., "Mechanism of Cell Damage by Ultrasound in Combination with Hematoporphyrin", *Japanese Journal of Cancer Research*, 81:962–966, Sep., 1990.

(List continued on next page.)

*Primary Examiner*—Mark Bockelman
(74) *Attorney, Agent, or Firm*—Fish & Richardson, P.C.

(57) ABSTRACT

A method for delivering compounds through epithelial cell layers using impulse transients is described. The method involves applying a compound to, e.g., the stratum corneum, of a patient and then inducing impulse transients to create transient increases in the permeability of epithelial tissue, thereby facilitating delivery of the compound across the epithelial cell layer.

18 Claims, 8 Drawing Sheets

OTHER PUBLICATIONS

Vivino et al., "Stable Cavitation At Low Ultrasonic Intensities Induces Cell Death and Inhibits $^3$H–TdR Incorporation by Con–A–Stimulated Murine Lymphocytes In Vitro", *Ultrasound in Medicine and Biology*, 11:751–759, 1985.

Yumita et al., "Synergistic Effect of Ultrasound and Hematoporphyrin on Sarcoma 180", *Japanese Journal of Cancer Research*, 81:304–308, Mar., 1990.

Berens et al., "Effect of Acoustic Shock Waves on Clonogenic Growth and Drug Sensitivity of Human Tumor Cells In Vitro", *The Journal of Urology*, 142:1090–1094, 1989.

Doukas et al., "Physical Factors Involved in Stress–Wave–Induced Cell Injury: The Effect of Stress Gradient", *Ultrasound In Medicine and Biology*, 21: 961–967, 1995.

Doukas et al., "Physical Characteristics and Biological Effects of Laser–Induced Stress Waves", *Ultrasound In Medicine and Biology*, 22:151–164, 1996.

Flotte et al., "Laser–tissue Interactions VI", *SPIE–The International Society for Optical Engineering*, 2391:202–207, 1995.

Gambilher et al., "Permealibilization of the Plasma Membrane of L1210 Mouse Leukemia Cells Using Lithotripter Shock Waves", *The Journal of Membrane Biology*, 141:265–275, 1994.

Holmes et al., The Combined Effects of Shock Waves and Cisplatin Therapy on Rat Prostate Tumors, *The Journal of Urology*, 144:159–163, 1990.

Lee et al., "Alteration of Cell Membrane By Stress Waves In Vitro", *Ultrasound in Medicine and Biology*, 22:1285–1293, 1996.

McAuliffe et al., "Stress–Wave–Assisted Transport Through the Plasma Membrane In Vitro", *Lasers in Surgery and Medicine*, 20:216–222, 1997.

Mitragotri et al., "A Mechanistic Study of Ultrasonically–Enhanced Transdermal Drug Delivery", *Journal of Pharmaceutical Sciences*, 84:697–706, Jun., 1995.

* cited by examiner

COMPOUND DELIVERY USING IMPULSE TRANSIENTS

This is a continuation of application No. 08/978,954 filed Nov. 26, 1997 now U.S. Pat. No. 6,251,099.

CROSS REFERENCE TO RELATED APPLICATION

This application claims priority from U.S. Provisional Application Ser. No. 60/031,882, filed Nov. 27, 1996, which is incorporated herein in its entirety.

STATEMENT AS TO FEDERALLY SPONSORED RESEARCH

This invention was made with Government support from funding awarded through the Department of Defense Medical Free Electron Laser Program, N00014-94-I-0927. The Government therefore has rights in the invention.

BACKGROUND OF THE INVENTION

This invention relates to the delivery of compounds through epithelial cell layers using impulse transients, i.e., stress waves.

Various methods have been employed for facilitating the delivery of pharmaceutical agents through the skin. One layer of the skin is the stratum corneum, which forms the outermost layer of the epidermis and is thought to act as the skin's primary barrier to molecular transport. It has a thickness of 10 to 15 μm and is composed of layers of corneocytes, with the layers varying in thickness from 10 to 50 cells. Corneocytes are keratin-filled cells that lack nuclei and cytoplasmic organelles. Intercellular regions of the stratum corneum are composed mostly of neutral lipids and comprise 5 to 21% of the stratum corneum volume.

One method of delivering drugs through the skin is iontophoresis, in which electric current applied to the surface of the skin increases the penetration of charged drugs (Singh et al., Med. Re. Rev., 13:569, 1993). However, the efficiency of drug delivery using this method depends on the ionization state of the drug. In addition, because iontophoresis uses high current densities, it can burn the skin (Singh et al., supra).

In another method, phonophoresis, a drug is delivered through intact skin using ultrasound (Skauen et al., Intern. J. Pharm., 20:235, 1984; Mitragotri et al., J. Pharmaceut. Sci., 84:697, 1995). However, the tensile component of ultrasound waves (negative pressure), which is always present in ultrasound waves, can cause tissue injury (Ter Haar, *Biological Effects of Ultrasound in Clinical Applications,* In Ultrasound: Its Chemical, Physical, and Biological effects, Suslick, ed., VCH Publishers, pp. 305–20; 1988). In addition, the method requires long exposure to deliver a therapeutic dose of the drug.

SUMMARY OF THE INVENTION

The invention is based on the discovery that high pressure impulse transients, e.g., stress waves (e.g., laser stress waves (LSW) when generated by a laser), with specific rise times and peak stresses (or pressures), can safely and efficiently effect the transport of compounds, such as pharmaceutical agents, through layers of epithelial tissues, such as the stratum corneum and mucosal membranes. The new methods can be used to deliver compounds of a wide range of sizes regardless of their net charge. In addition, impulse transients used in the methods avoid tissue injury.

The compounds that can be transported through epithelial tissue layers by the new methods include pharmaceutical compounds such as photosensitizers, anesthetic agents, polypeptides, nucleic acids, and antineoplastic agents such as cisplatin, and mixtures of compounds.

In general, the invention features a method of delivering a compound, e.g., an anesthetic, such as lidocaine, a hormone, such as insulin, an anti-neoplastic agent, or a nucleic acid, through an epithelial tissue layer by (a) mixing the compound with a coupling medium to form a compound-coupling medium mixture; (b) contacting a surface of the epithelial tissue layer with the compound-coupling medium mixture; and (c) propagating one or more impulse transients through the compound-coupling medium mixture to contact and enter the epithelial tissue layer, whereby the compound passes through the epithelial tissue layer.

Each impulse transient can be a broad-band compressive wave having a rise time of at least 1 ns and a peak pressure of at least 300 bar less than that which will damage tissues, e.g., about 2000 bar. In certain embodiments, the impulse transient can have a duration of about 100 ns to 1 microsecond. The impulse transient can be generated by exposing a target material to a pulsed laser beam. The method can be enhanced by adding a step of applying hydrostatic pressure.

In certain embodiments, a transparent material can be bonded to a surface of the target material to enable confined ablation. In other embodiments, the target material can be a metallic foil, e.g., of aluminum or copper, or a plastic sheet, e.g., of a polymer like polystyrene, and the impulse transient is generated by a laser-induced plasma formed by ablation of the target material. In another embodiment, the target material can be an absorbing material, and the impulse transient is generated by laser-induced rapid heating of the absorbing material.

In another aspect, the invention features an apparatus for delivering a compound through an epithelial tissue layer. The apparatus includes a reservoir for containing a coupling medium suitable for mixing with the compound, wherein the reservoir is arranged to enable the coupling medium to directly contact a surface of the epithelial tissue layer; and an energy source, e.g., a laser or lithotripter, arranged and controlled to propagate an impulse transient within the reservoir when filled with the coupling medium.

In another embodiment, the apparatus further includes a target material, e.g., a metal foil or plastic sheet, arranged between the laser and the reservoir, and the reservoir is configured to enable the target material to directly contact the coupling material in the reservoir. The apparatus can further include a transparent material bonded to a surface of the target material and interposed between the surface and the laser, and arranged to confine pressure forces resulting from ablation of the target material within the reservoir. The invention also features a system for delivering a compound through an epithelial cell layer in an animal. This system includes the apparatus and a coupling medium suitable for mixing with the compound.

The laser pulse can have a duration of about 10 to 70 nanoseconds (ns), or in certain embodiments, a duration of about 20 to 40 ns. About 1 to 10 laser pulses, and consequently 1 to 10 impulse transients, are applied to an epithelial cell layer during any one exposure period. In certain embodiments, about 1 to 3 laser pulses are applied.

The impulse transients can have a rise time of about 1 to 200 ns. Typically, the impulse transients can have a rise time of about 5 to 15 ns.

The impulse transients can have a peak stress or pressure of about 300 to 2000 bars, depending on the nature of the epithelial cell layer. In particular embodiments, the impulse transients can have a peak stress or pressure of about 500 to 1500 bars, e.g., about 550 to 650 bars.

The impulse transients can have a duration of about 100 ns to 1.1 microseconds ($\mu$s). In specific embodiments, the laser pulse can have a duration of about 150 to about 750 ns, or about 200 to about 300 ns.

An impulse transient is a broad-band, compressive wave having a peak pressure of up to about 2000 bar, and a fast, but not discontinuous, rise time (on the order of 200 ns or less). Accordingly, impulse transients are not shock waves, which are characterized by a discontinuous rise time. Further, an impulse transient is preferably a unipolar compressive wave, but in addition to the major compressive component, can include a minor tensile component that is less than 5 to 10% of the compressive peak pressure.

A coupling medium is a non-linear liquid or gel medium in which the impulse transients are generated and propagated. The coupling medium enables a direct contact of the impulse transients to the surface of the epithelial cell layer and minimizes acoustic reflections.

The coupling medium may optionally contain a surfactant to enhance delivery of the compound across the epithelial tissue, e.g., by increasing the time required for the epithelial tissue to become impermeable following generation of an impulse transient. The surfactant can be a detergent and thus can include, e.g., sodium lauryl sulfate, cetyl trimethyl ammonium bromide, and lauryl dimethyl amine oxide.

The invention has many advantages. In particular, the specific rise time and magnitude of the impulse transients used in the new methods induce a temporary permeability in epithelial tissue layers. This increases the diffusion of compounds through these layers for a short period of time, and allows effective delivery of the compounds such as drugs without causing destruction or killing of cells. Thus, the method can be used to deliver drugs to desired locations underlying epithelial cell layers. For example, impulse transients can be used to deliver chemotherapeutic agents to the site of a skin cancer lesion. In this manner, a host of maladies can be treated.

Moreover, drugs that have been previously dismissed because they could not be transported through epithelial tissue layers, e.g., the stratum corneum layer, can be delivered using the new methods. Similarly, the new methods can also be used to deliver drugs whose toxicity or high cost precludes or discourages systemic administration.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

Various features and advantages of the invention will be apparent from the following detailed description and from the claims.

DETAILED DESCRIPTION

Figure 1:
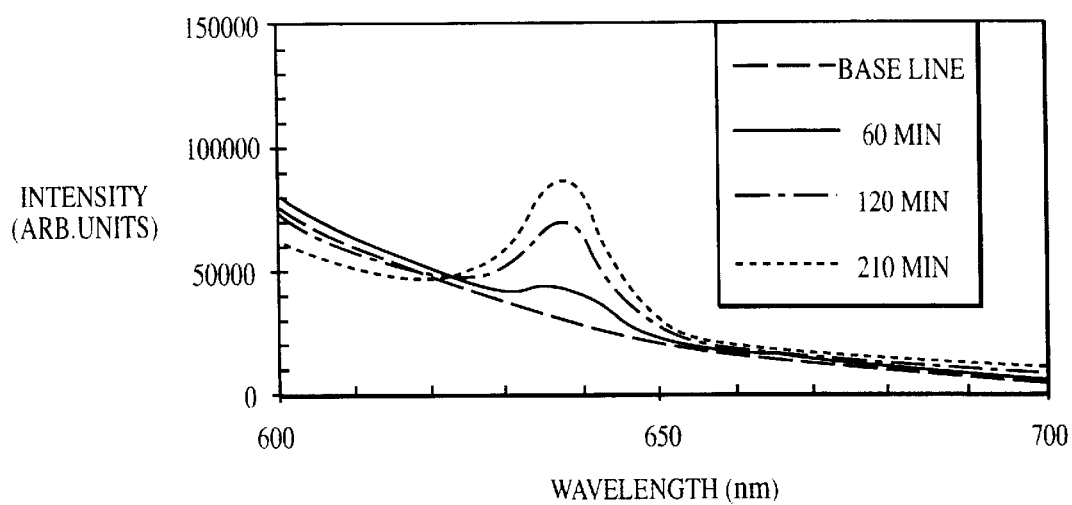
FIG. 1 is a graph illustrating the change in fluorescence of skin over time after the addition of 5-aminolevulenic acid (ALA) and a single impulse transient to the skin.

The invention provides new methods for delivering compounds, e.g., pharmaceutical compounds, through multiple cellular layers of epithelial tissue of a person or animal using impulse transients. Impulse transients induce a transient increase in the permeability of the epithelial tissue layer, thereby increasing diffusion of a compound from an exterior region of the epithelial tissue layer, through the epithelial tissue.

Prior to exposure to an impulse transient, an epithelial tissue layer, e.g., the stratum corneum or a mucosal layer, is likely impermeable to a foreign compound; this prevents diffusion of the compound into cells underlying the epithelial layer. Exposure of the epithelial layer to the impulse transients enables the compound to diffuse through the epithelial layer. The rate of diffusion, in general, is dictated by the nature of the impulse transients and the size of the compound to be delivered.

The rate of penetration through specific epithelial tissue layers such as the stratum corneum of the skin also depends on several other factors including pH, the metabolism of the cutaneous substrate tissue, pressure differences between the region external to the stratum corneum, and the region internal to the stratum corneum, as well as the anatomical site and physical condition of the skin. In turn, the physical condition of the skin depends on health, age, sex, race, skin care, and history, for example, prior contacts with organic solvents or surfactants.

The amount of compound delivered through the epithelial tissue layer will also depend on the length of time the epithelial layer remains permeable, and the size of the surface area of the epithelial layer which is made permeable.

Properties of Impulse Transients

The properties and characteristics of impulse transients are controlled by the energy source used to create them.

However, their characteristics are modified by the linear and non-linear properties of the coupling medium through which they propagate. The linear attenuation caused by the coupling medium attenuates predominantly the high frequency components of the impulse transients. This causes the bandwidth to decrease with a corresponding increase of the rise time of the impulse transient. The non-linear properties of the coupling medium, on the other hand, cause the rise time to decrease. The decrease of the rise time is the result of the dependence of the sound and particle velocity on stress (pressure). As the stress increases, the sound and the particle velocity increase as well. This causes the leading edge of the impulse transient to steepen.

The relative strengths of the linear attenuation, non-linear coefficient, and the peak stress determine how long the wave has to travel for the rise time steepening to become substantial. This distance can be calculated from the theory of non-linear acoustics (Lyamshev Sov. Phys. Usp., 24:977, 1981).

For a planar impulse transient, the distance (L) travelled through the coupling medium that leads to non-linear distortions is given by equation (1) (Lyamshev Sov. Phys. Usp. 24:977; 1981):

$$L = \frac{1 p c^2}{\varepsilon P} \quad (1)$$

where 1 is the spatial width of the rise time (temporal rise time multiplied by the sound velocity), p the density of the medium, c the sound velocity, $\varepsilon$ the non-linear coefficient and P the peak stress or pressure. If the coupling medium is water, for example, an impulse transient with a temporal rise time of 20 ns and peak pressure of 500 bar will show significant steepening within a propagation distance of about 1.5 mm.

The steepening can be calculated from equation (2):

$$\delta = \frac{p c v}{\varepsilon P} \quad (2)$$

where $\delta$ is the width of the rise time and v the dissipative coefficient (defined by equation 3):

$$v = \left( \frac{2 c^3}{\omega P} \right) \quad (3)$$

where $\omega$ is the frequency of the peak stress or pressure, and $\alpha$ is the absorption coefficient at frequency $\omega$.

The rise time, magnitude, and duration of the impulse transient are chosen to create a non-destructive (i.e., non-shock wave) impulse transient that temporarily increases the permeability of the epithelial tissue layer. Equations 1, 2, and 3, described above, can be used for calculating the parameters from published values for different coupling media. Generally, the rise time is at least 1 ns, and is more preferably about 10 ns.

The peak stress or pressure of the impulse transients varies for different epithelial tissue or cell layers. For example, to transport compounds through the stratum corneum, the peak stress or pressure of the impulse transient should be set to at least 400 bar; more preferably at least 1,000 bar, but no more than about 2,000 bar.

For epithelial mucosal layers, the peak pressure should be set to between 300 bar and 800 bar, and is preferably between 300 bar and 600 bar.

The impulse transients preferably have durations on the order of a few tens of ns, and thus interact with the epithelial tissue for only a short period of time. Following interaction with the impulse transient, the epithelial tissue is not permanently damaged, but remains permeable for up to about three minutes.

In addition, the new methods involve the application of only a few discrete high amplitude pulses to the patient. The number of impulse transients administered to the patient is typically less than 100, more preferably less than 50, and most preferably less than 10. If multiple optical pulses are used to generate the impulse transient, the time duration between sequential pulses is 10 to 120 seconds, which is long enough to prevent permanent damage to the epithelial tissue.

Properties of impulse transients can be measured using methods standard in the art. For example, peak stress or pressure, and rise time can be measured using a polyvinylidene fluoride (PVDF) transducer method as described in Doukas et al., Ultrasound Med. Biol., 21:961 (1995).

Generation of Impulse Transients

Impulse transients can be generated by various energy sources. For example, impulse transients can be generated by ablation or thermoelastic expansion of an appropriate target material by a high energy optical source such as a laser (Doukas et al., *Physical Characteristics and Biological Effects of Laser-Induced Stress Waves,* Ultrasound in Med. & Biol., 22:151–164, 1996). When impulse transients are generated by laser, they can be referred to as laser stress waves.

The efficiency of conversion of laser energy to mechanical energy of the impulse transient is given by the coupling coefficient of the target material. The coupling coefficient ($C_m$) is defined as the total momentum transfer to the target material during ablation divided by the pulse energy. The physical phenomenon responsible for launching the impulse transient is, in general, chosen from three different mechanisms: (1) thermoelastic generation; (2) optical breakdown; or (3) ablation.

For example, the impulse transients can be initiated by applying a high energy laser source to ablate a target material, and the impulse transient is then coupled to an epithelial tissue or cell layer by a coupling medium. The coupling medium can be, for example, a liquid or a gel, as long as it is non-linear. Thus, water, oil such as castor oil, an isotonic medium such as phosphate buffered saline (PBS), or a gel such as a collagenous gel, can be used as the coupling medium.

The coupling medium can in addition include a surfactant that enhances transport, e.g., by prolonging the period of time in which the stratum corneum remains permeable to the compound following the generation of an impulse transient. The surfactant can be, e.g., ionic detergents or nonionic detergents and thus can include, e.g., sodium lauryl sulfate, cetyl trimethyl ammonium bromide, and lauryl dimethyl amine oxide.

The absorbing target material acts as an optically triggered transducer. Following absorption of light, the target material undergoes rapid thermal expansion, or is ablated, to launch an impulse transient. Typically, metal and polymer films have high absorption coefficients in the visible and ultraviolet spectral regions.

Many types of materials can be used as the target material in conjunction with a laser beam, provided they fully absorb light at the wavelength of the laser used. The target material can be composed of a metal such as aluminum or copper; a plastic, such as polystyrene, e.g., black polystyrene; a ceramic; or a highly concentrated dye solution. The target material must have dimensions larger than the crosssectional area of the applied laser energy. In addition, the target material must be thicker than the optical penetration depth so that no light strikes the surface of the skin. The target material must also be sufficiently thick to provide mechanical support. When the target material is made of a metal, the typical thickness will be 1/32 to 1/16 inch. For plastic target materials, the thickness will be 1/16 to 1/8 inch.

Impulse transients can be also enhanced using confined ablation. In confined ablation, a laser beam-transparent material, such as a quartz optical window, is placed in close contact with the target material. Confinement of the plasma created by ablating the target material by using the transparent material increases the coupling coefficient by an order of magnitude (Fabro et al., J. Appl. Phys., 68:775, 1990). The transparent material can be quartz, glass, or transparent plastic.

Since voids between the target material and the confining transparent material allow the plasma to expand, and thus decrease the momentum imparted to the target, the transparent material is preferably bonded to the target material using an initially liquid adhesive, such as carbon-containing epoxies, to prevent such voids.

The laser beam can be generated by standard optical modulation techniques known in the art, such as by employing Q-switched or mode-locked lasers using, for example, electro or acousto-optic devices. Standard commercially available lasers that can operate in a pulsed mode in the infrared, visible, and/or infrared spectrum include Nd:YAG, Nd:YLF, $CO_2$, excimer, dye, Ti:sapphire, diode, holmium (and other rare-earth materials), and metal-vapor lasers. The pulse widths of these light sources are adjustable, and can vary from several tens of picoseconds (ps) to several hundred microseconds. For use in the new methods, the optical pulse width can vary from 100 ps to about 200 ns and is preferably between about 500 ps and 40 ns.

Impulse transients can also be generated by extracorporeal lithotripters (one example is described in Coleman et al., Ultrasound Med. Biol., 15:213–227, 1989). These impulse transients have rise times of 30 to 450 ns, which is longer than laser-generated impulse transients. To form an impulse transient of the appropriate rise time for the new methods using an extracorporeal lithotripter, the impulse transient is propagated in a non-linear coupling medium (e.g., water) for a distance determined by equation (1), above. For example, when using a lithotripter creating an impulse transient having a rise time of 100 ns and a peak pressure of 500 barr, the distance that the impulse transient should travel through the coupling medium before contacting an epithelial cell layer is approximately 5 millimeters (mm).

An additional advantage of this approach for shaping impulse transients generated by lithotripters is that the tensile component of the wave will be broadened and attenuated as a result of propagating through the non-linear coupling medium. This propagation distance should be adjusted to produce an impulse transient having a tensile component that has a pressure of only about 5 to 10% of the peak pressure of the compressive component of the wave. Thus, the shaped impulse transient will not damage tissue.

The type of lithotripter used is not critical. Either a electrohydraulic, electromagnetic, or piezoelectric lithotripter can be used.

The impulse transients can also be generated using transducers, such as piezoelectric transducers. Preferably, the transducer is in direct contact with the coupling medium, and undergoes rapid displacement following application of an optical, thermal, or electric field to generate the impulse transient. For example, dielectric breakdown can be used, and is typically induced by a high-voltage spark or piezoelectric transducer (similar to those used in certain extracorporeal lithotripters, Coleman et al., Ultrasound Med. Biol., 15:213–227, 1989). In the case of a piezoelectric transducer, the transducer undergoes rapid expansion following application of an electrical field to cause a rapid displacement in the coupling medium.

In addition, impulse transients can be generated with the aid of fiber optics. Fiber optic delivery systems are particularly maneuverable and can be used to irradiate target materials located adjacent epithelial tissue layers to generate impulse transients in hard-to-reach places. These types of delivery systems, when optically coupled to lasers, are preferred as they can be integrated into catheters and related flexible devices, and used to irradiate most organs in the human body. In addition, to launch an impulse transient having the desired rise times and peak stress, the wavelength of the optical source can be easily tailored to generate the appropriate absorption in a particular target material.

Delivery of Compounds Using Impulse Transients

Because impulse transients exert physical forces to increase the permeability of the epithelial tissue, they can be used to transport many different types of compounds. Thus, chemotherapeutic agents such as cisplatin, polypeptides, such as antibodies, nucleic acids, such as oligonucleotides, DNA, RNA, and plasmids, local anesthetics, such as lidocaine and benzocaine, and photosensitizers, such as benzoporpherene derivative monoacid ring A (BPD-MA), all can be delivered through epithelial tissue layers, e.g., transdermally, using impulse transients. The compounds may optionally be heated prior to generation of the impulse transient to facilitate their transport through the skin.

Localization of the compound using the methods of the invention is advantageous, as it allows impulse transients to be administered with highly localized effects to areas of diseased cells, thus sparing the other tissues of the body. In this way, healthy tissues and organs are spared from adverse effects of a systemically administered drug.

Compounds which have a toxic effect at higher dosages can be administered to a patient using guidelines for administration that will produce greater concentrations of the drugs in the treated tissues or cells compared to the surrounding tissues, while maintaining adequate levels of the drug in these treated tissues or cells. In general, this differential drug localization can be achieved using guidelines for administration determined using standard techniques known in the field of pharmacology. Preferably, the compound dosage and time course are such that a 2:1 or greater concentration ratio is achieved in the treated tissues or cells compared to the surrounding, untreated tissues.

Determining the appropriate dosage for a specific compound, and for a particular subject or patient (human or animal) is a routine matter to one skilled in the art of pharmaceutical administration. Two approaches are commonly used to assay directly the quantity of drug in the diseased (treated) and surrounding tissues. First, tissue samples are obtained from animals (e.g., pigs) or patients who have been treated with different dosage and timing protocols. Cadaver skin samples can also be used in this assay. The quantity of drug in each tissue is then measured either chemically, or if there is a unique optical signal such as fluorescence, then by quantitative microscopy or laser-induced fluorescence. The results are tabulated to determine a scale of optimum drug dosages and types of impulse transients for a given epithelial tissue layer, body region, and compound.

The compound or compounds to be delivered through an epithelial cell layer are administered by mixing the compound with the coupling medium, and applying the coupling medium-compound mixture to the surface of the epithelial cell layer, e.g., the stratum corneum, in the region in which transport is desired. The compound must be thoroughly dispersed in, and is preferably dissolved in, the coupling medium. Thus, hydrophilic compounds can be mixed with an aqueous coupling medium, and hydrophobic compounds can be mixed with an oil-based coupling medium.

Once the target material and coupling medium in a container are set in position on a particular region of the surface of an epithelial tissue layer, impulse transients are used to permeabilize the epithelial tissue layer in the region in which the coupling medium directly contacts the cell layer, using the methods described herein. The methods result in the delivery of the compounds to the cells underlying the epithelial tissue layer in the region of interest that normally would not cross the epithelial tissue layer barrier.

Hydrostatic pressure can be used in conjunction with impulse transients to enhance the transport of a compound through the epithelial tissue layer. Since the effects induced by the impulse transients last for several minutes, the transport rate of a drug diffusing passively through the epithelial cell layer along its concentration gradient can be increased by applying hydrostatic pressure on the surface of the epithelial tissue layer, e.g., the stratum corneum of the skin, following application of the impulse transient. This method is described in further detail in the examples below. The hydrostatic medium can be any liquid, such as water or phosphate buffered saline.

Topical application and delivery of compounds by the new methods allow the compounds to be localized to a site of interest. Thus, the compound, e.g., a drug, is more concentrated at the site of action and has a minimal, if any, systemic concentration. This enhances the therapeutic effect of the drug and simultaneously minimizes systemic side-effects. Another advantage compared to systemic administration is that compounds transported through epithelial tissue bypass systemic deactivation or degradation (e.g., hepatic "first-pass" effects). Gastrointestinal incompatibility and potential toxicological risks are also minimized relative to systemic administration. In addition, drugs developed for topical application can be designed so that they are deactivated systematically (i.e., the "soft drug" concept), using standard techniques. Topical administration may also be desired when the compound is rare or expensive.

EXAMPLES

The following examples are used to describe the delivery of compounds using impulse transients.

Example 1

Transdermal Delivery of ALA 5-aminolevulenic acid (ALA) was used as a compound to demonstrate the permeation effect of impulse transients on the stratum corneum. ALA is converted in cells to protoporphyrin IX, which fluoresces at 634 nm (405 nm excitation), while ALA does not fluoresce. Thus, the transport of ALA can be followed, non-invasively, by monitoring the fluorescence of the skin. In addition, since the conversion of ALA to protophyrin IX requires that cells be viable, the measurement of protophyrin IX fluorescence also assays cell viability in vivo.

For these experiments, a Q-switched solid state ruby laser (20 ns pulse duration, capable of generating up to 2 joules per pulse) was used to generate the laser beam, which hit the target material (black polystyrene sheet about 1 mm thick) and generated a single impulse transient. Impulse transients of up to 1000 bar peak stress and 50 ns duration and with a ½ inch beam diameter can be generated with this laser-target system. The large target ensures that the impulse transients generated are plane waves, because the thickness of the coupling medium is much shorter than the diameter of the impulse transient. An articulating arm was used and the laser path was totally covered for safety.

A plastic (flexible) washer approximately 1 inch in diameter and ¹⁄₁₆ inches thick was used as a reservoir for the sample solution (5% concentration of the ALA in PBS coupling medium) to be delivered through the stratum corneum. The washer was attached onto the skin with grease. The sample filled the central opening of the washer, which was approximately ¼ inch in diameter. The target material was positioned on top of the washer and irradiated with 1 laser pulse.

The black polystyrene target completely absorbed the laser radiation so that the skin was exposed only to impulse transients, and not laser radiation. The impulse transients, even at the highest peak stress of 1,000 bar, did not produce any pain in the subject. After exposure to the impulse transients, the excess ALA solution was removed. The skin was monitored for fluorescence of protophyrin IX thirty minutes after exposure to the impulse transients. The fluorescence intensity increased for approximately 4 hours, at which point it reached the maximum intensity and subsequently decreased.

FIG. 1 shows the change of fluorescence intensity at different wavelengths over time after the application of a single impulse transient. As shown in the graph, the peak in intensity occurs at about 640 nm and is highest after 210 minutes (dashed line) post-treatment.

Figure 2:
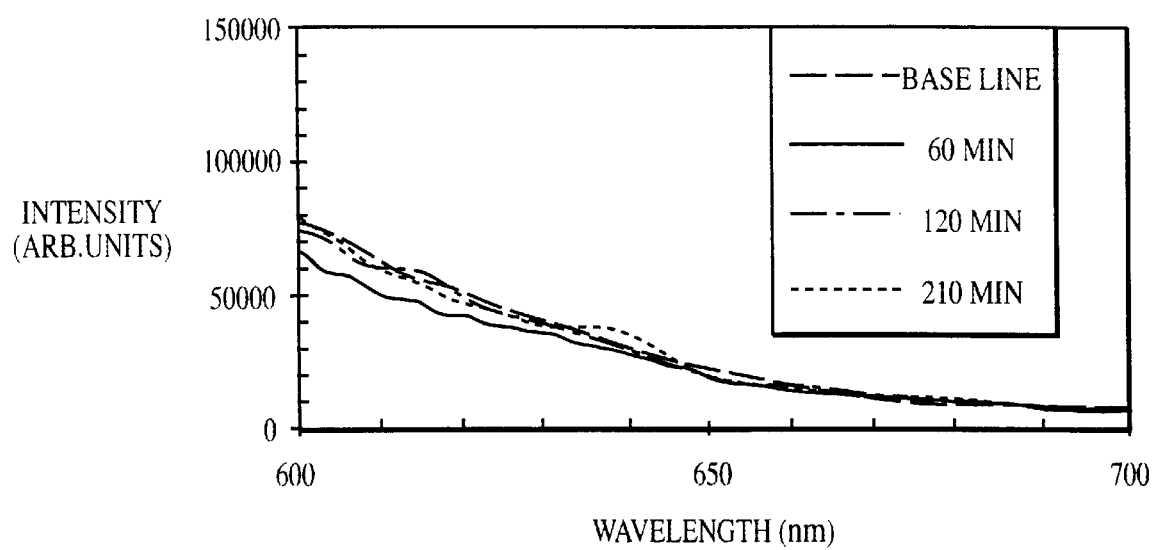
FIG. 2 is a graph illustrating the change in fluorescence of skin over time after the addition of ALA to the skin without an impulse transient.

FIG. 2 shows the fluorescence from an adjacent site (control) where ALA was applied without any impulse transients. As shown in this graph, there is little change in the intensity at different time points.

Figure 3:
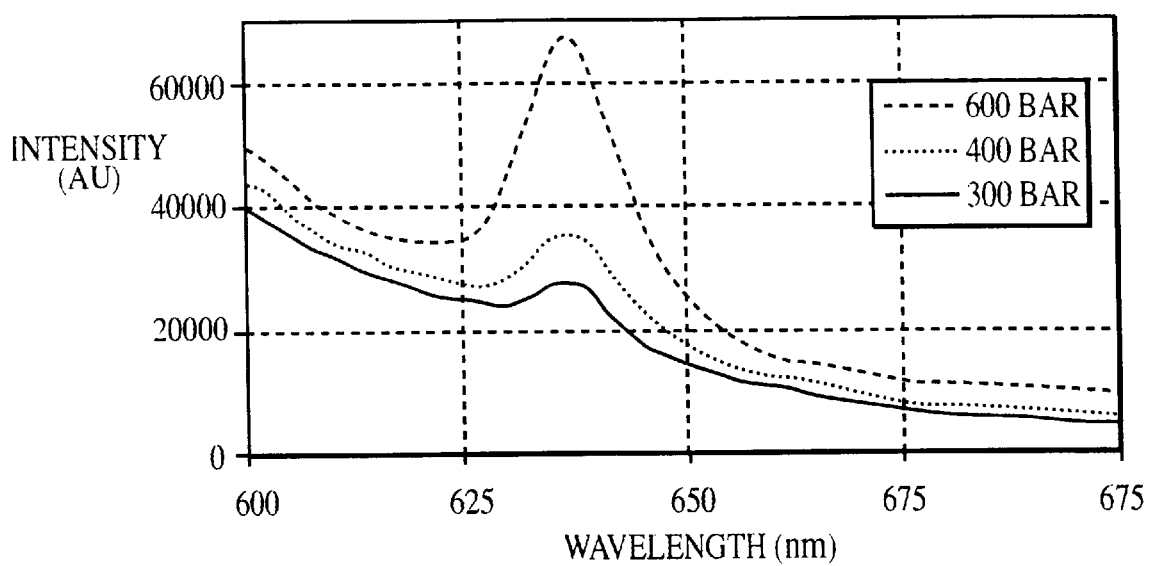
FIG. 3 is a graph illustrating the comparative changes in fluorescence of skin following the addition of ALA and a single impulse transient under the indicated peak stresses.

FIG. 3 shows the effects of varying the applied peak stress of the impulse transient on ALA transport. As shown in the graph, the degree of permeabilization of the stratum corneum depends on the peak stress. In three separate experiments, a single impulse transient was applied at 500 mJ, 600 mJ, or 1 J to generate applied peak stresses of 300 bar, 400 bar, and 600 bar, respectively. FIG. 3 shows that protophyrin IX fluorescence increased with increasing peak pressure, demonstrating that transdermal transport of ALA increases with increasing peak stress. The onset of the permeabilization of the stratum corneum was observed above 300 bar.

The permeabilization of the stratum corneum is transient. When sites on the stratum corneum were exposed first to impulse transients and ALA was then applied on the same sites after 5 minutes, no fluorescence emission from protophyrin IX was observed. Therefore, the permeabilization of the stratum corneum lasted less than 5 minutes.

Penetration of ALA through the skin (without the action of impulse transients) depends on many conditions, such as skin hydration, skin temperature, anatomical site, condition of skin and contact time. All fluorescence measurements were compared to the fluorescence emission of the target site on the stratum corneum before the experiments.

Example 2

Transdermal Delivery of 40 kDa Dextran and 20 nm Latex Particles

The ability of impulse transients to deliver large macromolecules across the stratum corneum was determined using probes of rhodamine B dextran having a molecular weight of 40 kDa and a diameter of about 8.8 nm, and fluorescent latex particles 20 nm in diameter.

Ten-week old male fuzzy rats, each having a mass of 300–400 g, were obtained from Harlan-Sprague-Dawley (Indianapolis, Ind.) and acclimated for a minimum of 48 hours prior to use. Animals were anesthetized by intramuscular injection of ketamine (120 mg/kg), xylazine (20 mg/kg), and atropine (0.04 mg/kg).

A single laser pulse was delivered to the target material, which generated a single impulse transient. Aqueous probe solutions of 500 $\mu$M rhodamine B dextran of 40 kDA molecular weight (Molecular Probes, Eugene, Oreg.) or 2% (weight/volume) fluorescent latex particles, 20 nm in diameter (Molecular Probes, Eugene, Oreg.) were allowed to remain in contact with the skin for five minutes after the application of the impulse transient. Subsequently, the solution was removed and the surface of the skin was cleaned with water. Control sites adjacent to the sites exposed to impulse transients were treated with the donor solution in an identical manner except that they were not exposed to impulse transients. In addition, some control sites were exposed to a impulse transient using sterile water only as the coupling medium.

A flexible washer approximately 19 mm in diameter was used as a reservoir for the donor solution to be delivered through the stratum corneum. The washer was attached on the skin on the dorsal side of each rat with grease, and a black polystyrene target material was placed on top of the washer in contact with the solution. The solution acted as the acoustic coupling medium.

Impulse transients were generated by ablation of the target material (Perri, Phys. Fluids 16:1435–1440, 1973) with a 23 nsec pulse from a Q-switched ruby laser and launched into the reservoir containing the molecular probe solution. An articulated arm was used to deliver the beam to the target. The beam size at the target was about 6 mm in diameter to achieve a fluence of about 7 J/cm$^2$. The laser pulse was completely absorbed by the target so that only the impulse transient propagated through the probe solution and impinged onto the skin of the rat. The impulse transients were measured in separate experiments under identical conditions of laser parameters, target material, and propagation distance through the coupling medium with a calibrated polyvinylidene fluoride transducer (Doukas et al. Ultrasound Med. Biol. 21:961–967, 1995).

Figure 4:
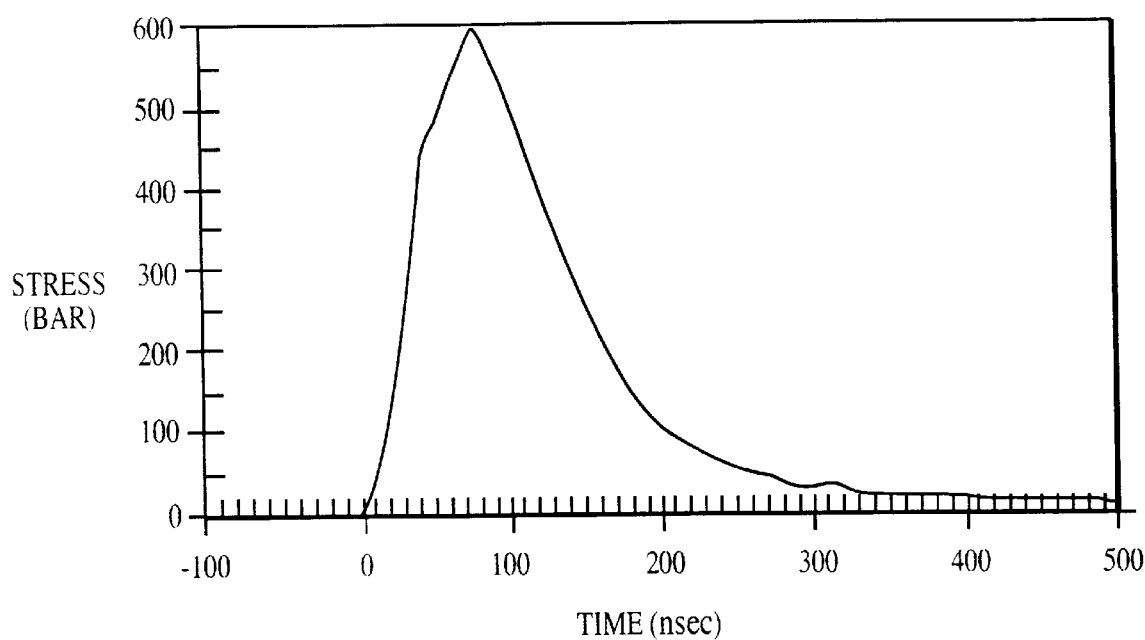
FIG. 4 is a graph illustrating the waveform of an impulse transient generated by ablation of a black polystyrene target with a single 23 nsec Q-switched ruby laser pulse.

The temporal profile of the impulse transients used in these experiments is shown in FIG. 4. The peak stress in the skin ($P_s$) was calculated from the peak pressure in water ($P_w$) and the acoustic impedance of water ($Z_w$=1.48×10$^6$ kgm$^{-2}$s$^{-1}$) and skin ($Z_s$=1.54×10$^6$ kgm$^{-2}$s$^{-1}$) (Payne et al., Sound Skin Models-Acoustic Properties of Epidermis and Dermis. In Skin Models To Study Function and Disease of Skin. Parks et al., ed., Springer Verlag, Berlin, pp. 402–411; 1986) using the equation $P_s/P_w=2Z_w/(Z_s Z_w)$. The peak stress on the skin in all experiments was calculated to be 589±23 bar.

The delivery of the dextran and latex beads across the stratum corneum following the generation of impulse transients was observed using transmission photomicrographs and fluorescence emission spectra of biopsy samples. For these studies, skin samples were obtained one hour post-treatment using a 6 mm biopsy punch. Biopsies were embedded in OCT 4583™ (Sakura Finetek USA, Torrence, Calif.) and frozen. The skin samples were then sectioned in a cryostat microtome, and microphotographs were obtained with a Zeiss inverted microscope using a Rhodamine B filter set (XF39, Omega Optical, Brattleboro, Vt.). Fluorescence emission spectra of the exposed and control sites were collected from another group of animals while they were alive and under full anesthesia using a fiber-based fluorimeter (FLUORMAX™, Spex Industries, Edison, N.J.).

Figure 5A:
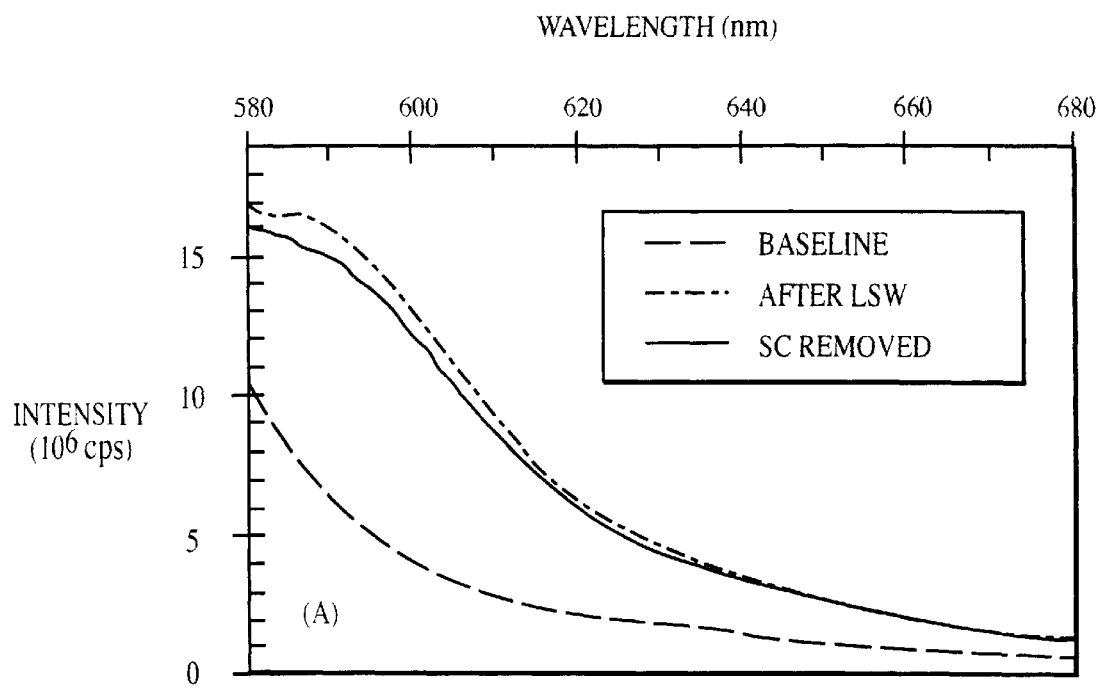
FIGS. 5A and 5B are graphs illustrating the fluorescence spectra (excitation: 486 nm) before generation of an impulse transient (baseline), immediately after exposure to the impulse transient (laser stress wave "LSW") in the presence of 40 kDa dextran (after LSW) and after the stratum corneum was removed by tape stripping ("SC removed") (FIG. 5A; and of the emission spectra of the exposed (+LSW) and control (−LSW) sites after subtraction of baseline fluorescence (FIG. 5B).

Transmission photomicrography revealed that rhodamine B dextran penetrated to a depth of approximately 50 $\mu$m into the skin. Fluorescence spectra also demonstrated that the rhodamine dextran penetrated the stratum corneum following induction of an impulse transient. The fluorescence emission spectra of skin exposed to a single impulse transient in the presence of 40 kDa dextran is shown in FIG. 5A. Emission spectra were taken at three different times: (1) before application of the dextran probe and generation of the impulse transient, in order to establish the baseline fluorescence (shown as the dashed line marked "baseline"), (2) immediately after generation of the impulse transient (shown as the broken line labeled "after LSW," for laser stress wave), and (3) after the stratum corneum of the exposed site was removed by tape stripping (shown as the solid line marked "SC removed"). Tape stripping was performed to eliminate the fluorescence from the probe molecules located in the stratum corneum. Thus, the fluorescence signal in the tape stripping experiment represented only the probe molecules located in the viable epidermis and dermis. Twenty tape strippings were sufficient to remove the stratum corneum (Wells, Br. J. Dermatol. 108:87–91, 1957). The data shown in FIG. 5A represent raw fluorescence.

The spectra shown in FIG. 5A indicate that rhodamine-associated fluorescence increased following delivery of an impulse transient to skin exposed to the 40 kDa rhodamine dextran probe (spectra labeled "after LSW"). Most of this fluorescence remained after removal of the stratum corneum (compare the spectra labeled "SC removed" with "after LSW"). Both of these spectra show significantly higher intensity than that shown by the baseline spectra. In addition, exposure of skin to impulse transients only did not induce any change in the fluorescence emission of the skin (data not shown). These data suggest that application of an impulse transient (in the form of a laser stress wave) caused the 40 kDa rhodamine dextran probe to be transported into the dermis, i.e., to be localized in tissues that are not sensitive to procedures that remove the stratum corneum.

Figure 5B:
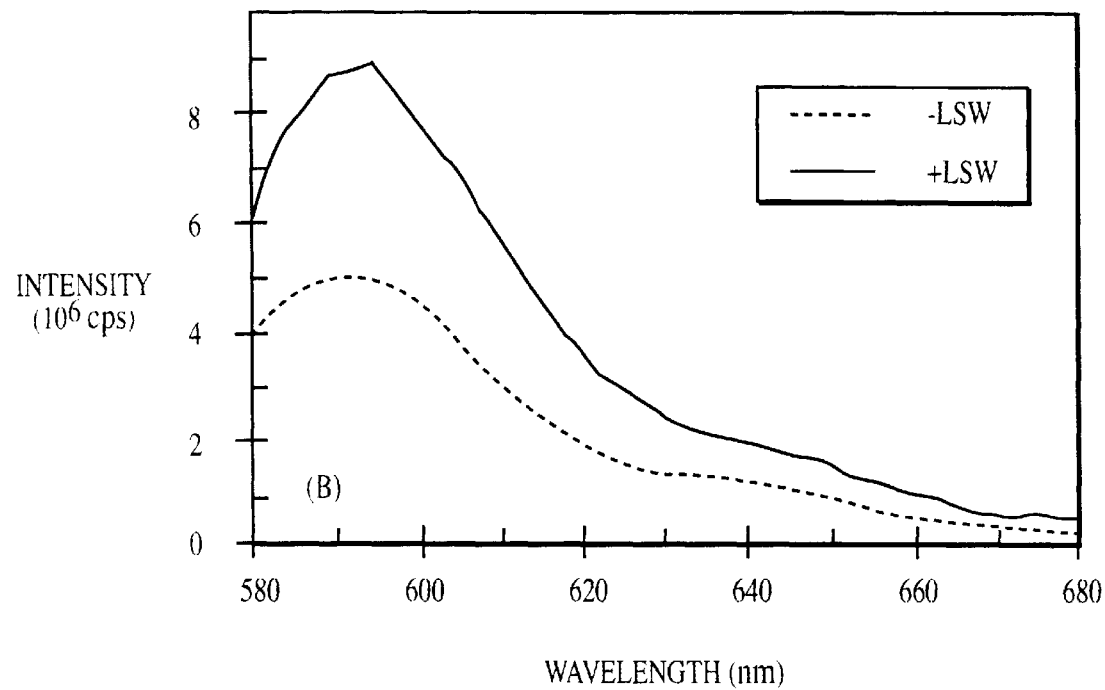

FIG. 5B shows the comparative fluorescence of sites exposed to the LSW (+LSW) and control sites (−LSW) after tape stripping and after the baseline fluorescence has been subtracted. The site subjected to an impulse transient showed over two-fold higher rhodamine associated fluorescence than the control site, which also demonstrates that impulse transients promote transport of the dextran probe across the stratum corneum.

Figure 6:
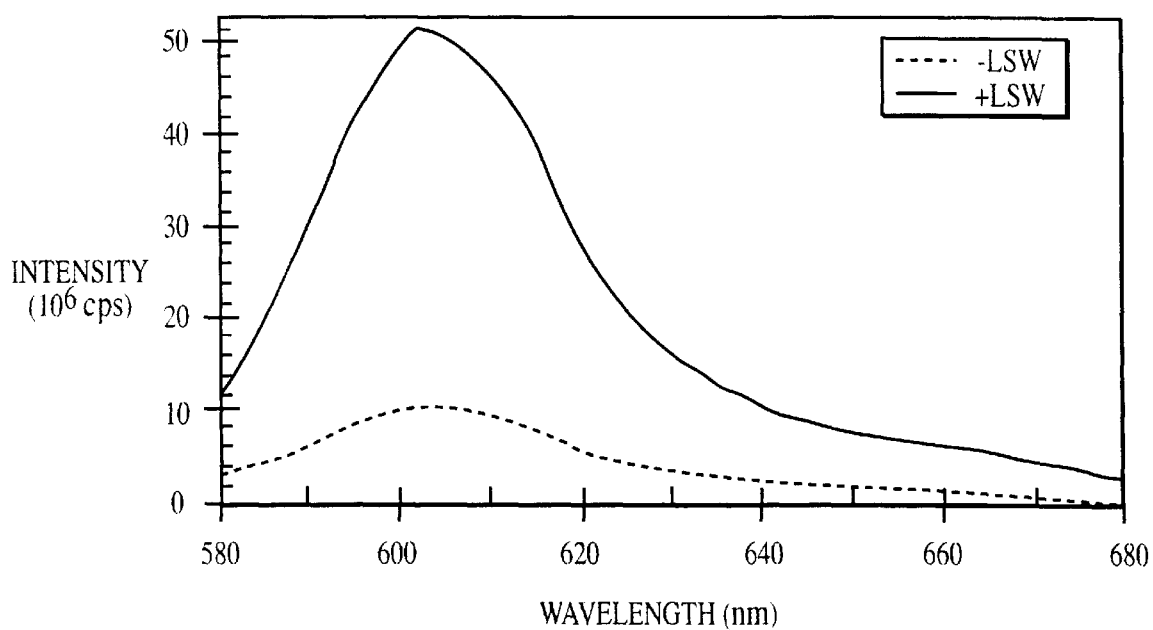
FIG. 6 is a graph illustrating the fluorescence spectra (excitation: 568 nm) of a site exposed to an impulse transient wave using 20 nm latex particles as the probe material (+LSW) and the control site (−LSW).

Latex fluorescent particles of 10 nm diameter were also delivered through the stratum corneum using impulse transients. FIG. 6 shows the fluorescence emission spectra after tape stripping of a site exposed to a impulse transient using latex particles as the fluorescent probe. The fluorescence emission of the control site under identical conditions is shown for comparison.

To measure the amount of time required for the stratum corneum to regain its barrier function for a probe molecule having the size of 40 kDa dextran, a single impulse transient was applied to skin using sterile water as the acoustic coupling medium. The coupling medium was immediately removed, and the probe solution added to the reservoir 2 minutes after the application of the impulse transient. The fluorescence emission spectra were then measured as described above. No fluorescence was detected. This indicates that the stratum corneum becomes impermeable to 40 kDa dextran within 2 minutes after the generation of the impulse transient.

Example 3

Transdermal Delivery Using Surfactants in the Coupling Medium

Figure 7:
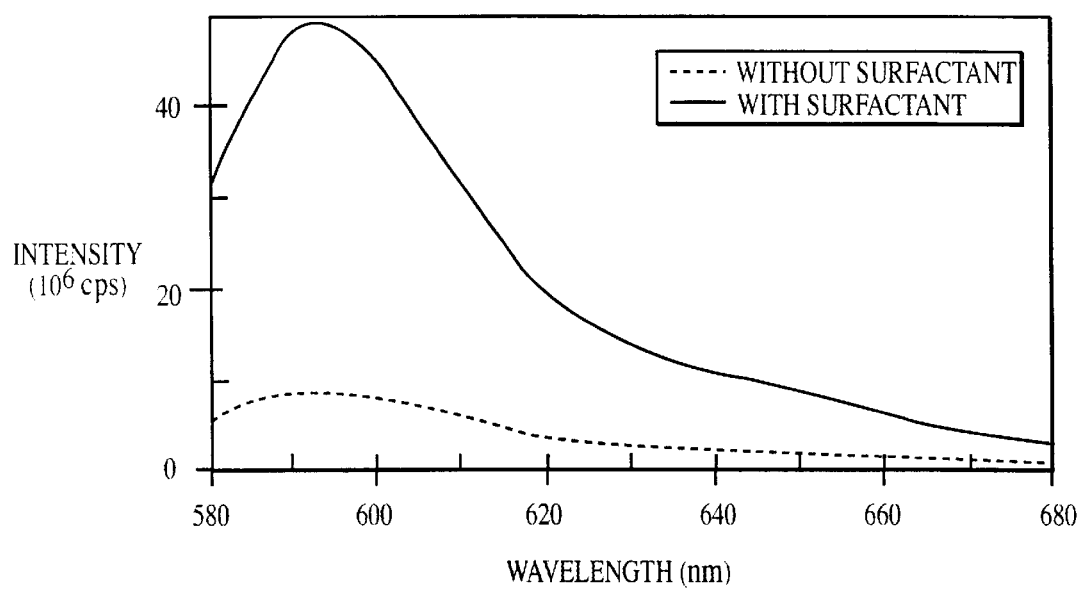
FIG. 7 is a graph illustrating the fluorescence spectra (excitation: 568 nm) of two sites exposed to an impulse transient using 40 kDA dextran as the probe in the presence (solid line) and absence (dashed line) of a surfactant.

The effect of a surfactant was examined by using a solution of 2% sodium lauryl sulfate (SLS) as the coupling medium. FIG. 7 shows the fluorescence spectra (from which baseline fluorescence had been subtracted) of the 40 kDa dextran probe molecule in skin at two sites at which an impulse transient had been generated. At one site (solid line), 2% SLS was used as the coupling medium; at the other, no SLS was added (dashed line). The two skin sites were tape stripped prior to generating the two spectra shown in FIG. 7.

A comparison of the spectra shown in FIG. 7 reveals that the fluorescence intensity of 40 kDa dextran was approximately 8–9 fold greater when 2% SLS was used in the coupling medium. Thus, a surfactant can significantly increase the amount of an agent delivered across the stratum corneum using an impulse transient.

To determine if surfactants in the coupling medium affect transport by increasing the time of recovery of the barrier function of the stratum corneum, the length of time to restore the barrier function of the stratum corneum was compared using water or an aqueous solution of 2% sodium lauryl sulfate (SLS) as the coupling medium.

As discussed above in Example 2, the stratum corneum becomes impermeable to the 40 kDa dextran probe within two minutes after generation of an impulse transient. To determine the length of time the stratum corneum remains permeable when impulse transients are generated in the presence of a surfactant, a single pulse was applied in which the initial coupling medium was an aqueous solution of 2% SLS. The surfactant was removed, and the aqueous solution of the 40 kDa dextran probe was added 15, 30, 45, and 60 minutes after generation of the impulse transient. The presence of the probe was then measured.

Probe molecules added as long as 45 to 60 minutes after generation of the impulse transient emitted fluorescence that was resistant to procedures that remove the stratum corneum. These observations indicate that when the surfactant was used in the coupling medium, the recovery of the barrier function of the stratum increased to 45–60 minutes. This compares to recovery of the barrier function within 2 minutes without the surfactant. Surfactants therefore can act to increase the time required for the stratum corneum to regain its barrier function.

Example 4

Transdermal Delivery of Anti-neoplastic Agents 5-fluorouracil (5-FU) is dissolved in an aqueous solution of PBS, which serves as the coupling medium, and applied to a skin cancer lesion in a suitable container as described in Example 1. A black polystyrene sheet is used as the target material and is placed on the container in direct contact with the coupling medium, which in turn transmits the impulse transients to the surface of the lesion. Five pulses from a Q-switched solid state ruby laser (1 J, 20 ns pulse duration) are applied to generate 5 separate impulse transients. The amount of 5-FU dissolved in the PBS is determined using standard techniques described herein and based on the nature of the lesion, the desired drug concentration in the lesion, and the patient's skin type.

Example 5

Transdermal Delivery of ALA Using Impulse Transients and Confined Ablation

In confined ablation, a transparent material is placed in close contact with the target material. Confinement of the plasma increases the coupling coefficient by an order of magnitude.

A quartz optical window with a thickness of ⅜ inch is used as the transparent material, and a black polystyrene sheet is used as the target material. To eliminate microscopic voids, a solvent is used to dissolve the surface of the polystyrene to allow it to bond to the quartz transparent material. This combined transparent material and target material is used in the same way as the target material in Example 1.

Plasma confinement causes an increase in the rise time of the impulse transient, which may decrease the effectiveness of the impulse transient. To counteract this effect, the distance the impulse transient propagates through the coupling medium is increased to shape the impulse transient to have an appropriate rise time when it contacts the surface of the epithelial tissue layer. The non-linear properties of the coupling medium cause the rise time to decrease. An impulse transient of 500 bar propagating through 1 mm of water undergoes a decrease in the rise time from 30 ns to 15 ns. Therefore, the initial increase of the rise time due to confinement can be compensated by appropriately adjusting the propagation length of the impulse transient through the reservoir.

The impulse transient is measured in separate experiments under identical conditions using a calibrated polyvinylidene fluoride transducer as described in Doukas et al., Ultrasound Med. Biol., 21:961 (1995). The temporal resolution of the combination of the transducer and oscilloscope is 5 ns. The pressure in the skin $P_s$ is calculated from the pressure in water $P_w$ and the acoustic impedances of water ($Z_w$) and skin ($Z_s$) using the equation $P_s/P_w = 2 Z_w/(Z_s+Z_w)$.

Impulse transients are generated by using one pulse of a Q-switched ruby laser (4 J, 30 ns). An ArF excimer laser can also be used (650 mJ, 25 ns). Transcutaneous delivery of ALA is measured by measuring protophyrin IX fluorescence as described above.

Example 6

Figure 8:
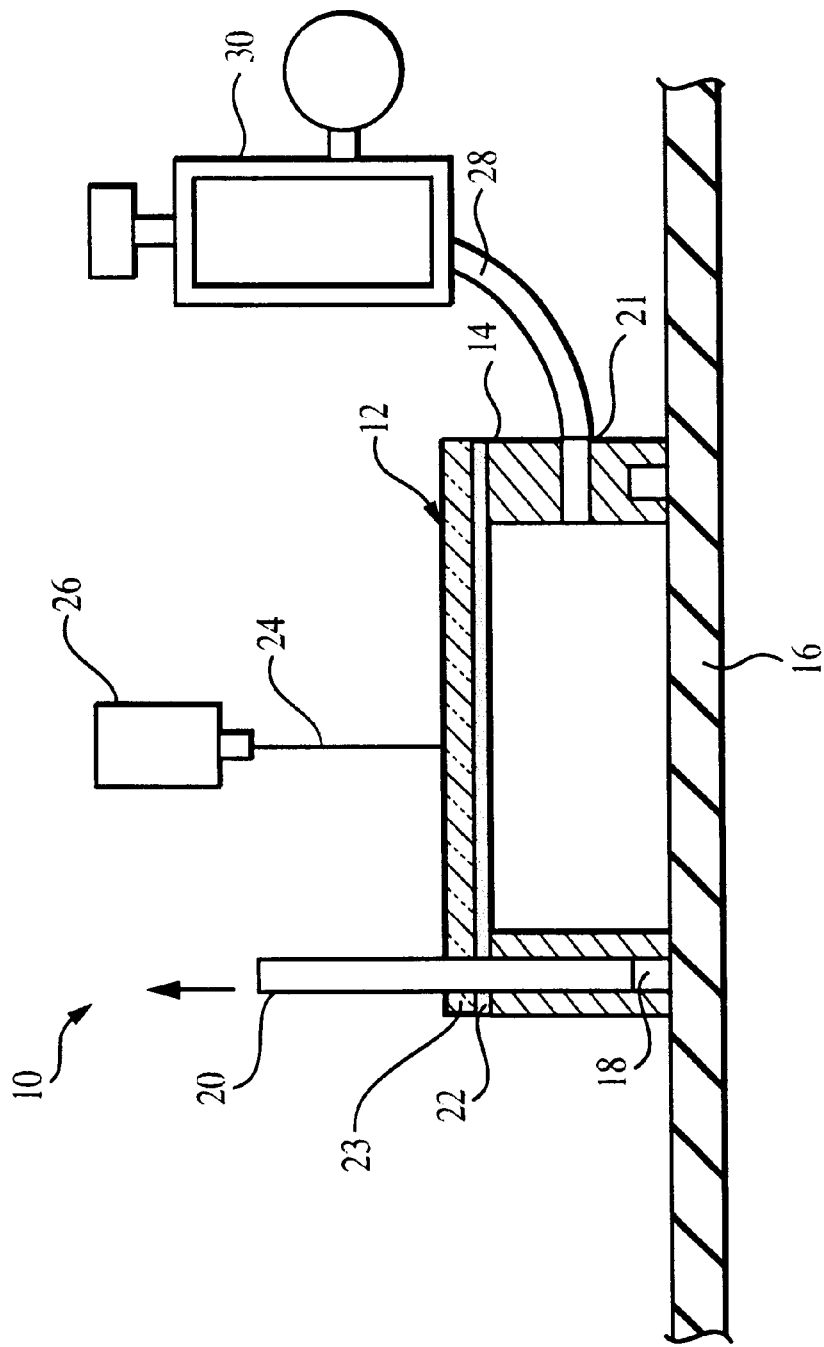
FIG. 8 is a schematic drawing of a device using hydrostatic pressure to enhance delivery of a compound through the stratum corneum following the application of an impulse transient.

Transdermal Delivery of Benzoporpherene Derivative Monoacid Ring A (BPD-MA) Using Impulse Transients and Hydrostatic Pressure FIG. 8 shows a schematic diagram of a device 10 that is used to control drug delivery by varying the hydrostatic pressure. A reservoir 12 is made from a plastic washer 14 about 3 mm in height and 1 cm in diameter and is attached to rabbit skin 16 with silicon grease. An outlet 20 that connects to a groove 18 in the bottom of the washer is connected to a suction pump (not shown). This allows the washer to remain firmly vacuum sealed on the skin during the application of hydrostatic pressure. A black polystyrene target material 22 is attached to the surface of the washer 14, and a quartz overlay 23 is placed on the target material. Laser radiation 24 from Q-switched ruby laser (4 J, 30 ns) 26 is directed onto the target material 22 using an articulating arm (not shown). A tube 28 is connected to an opening 21 in the side of the washer 14. The tube 28 is connected to a pressure regulator 30, and the reservoir 12 is filled with a solution of benzoporpherene derivative monoacid ring A (BPD-MA).

The fur on the back of a New Zealand albino rabbit is removed. The animal is anesthetized and the device 10 for applying hydrostatic pressure is attached to the back of the animal. Subsequently, hydrostatic pressure is applied and a single impulse transient is generated. The hydrostatic pressure is applied for 5 minutes. The device is then removed, the skin cleaned, and the fluorescence is measured using a fiber-based spectrofluorimeter (450 nm excitation, 650–750 nm emission).

These measurements are compared to three control sites in which BPD-MA is applied. One site is exposed to a single impulse transient with no hydrostatic pressure applied. The second is exposed only to hydrostatic pressure and no impulse transient, and the third is exposed to neither an impulse transient nor hydrostatic pressure.

The fluorescence measurements indicate the amount of BPD-MA present in the skin. To confirm these measurements, BPD-MA is extracted from the tissue and measured using standard techniques. Briefly, skin biopsies are weighed, mixed with 1 ml dimethyl sulfoxide (DMSO) and homogenized. The homogenized samples are kept at room temperature overnight and then centrifuged. The integrated fluorescence of the supernatant is measured in a spectrofluorimeter and the amount of drug is estimated from a calibration curve.

Example 7

Transdermal Delivery of a Compound Using a Lithotripter

A subject places a limb having the desired target area of skin into a water bath. The target area is covered by a small reservoir containing a 5% ALA solution in PBS. This reservoir differs from others described above in that it is covered on the side opposite the skin with a thin plastic film or membrane that has an impedance near that of water, i.e., it is designed not to reflect impulse transients generated by the lithotripter that propagate first through the water and then through the reservoir to reach the target epithelial layer. The ALA-PBS solution in the reservoir serves as both a source of the compound (ALA) and the coupling medium.

Ten pulses from a electrohydraulic lithotripter are applied in the water bath to generate ten impulse transients. The rise times and peak stress are adjusted to be about 5 to 15 ns and 500 bar, respectively, at the point of contact with the skin, following propagation through the water bath and the coupling medium.

Transdermal delivery of ALA is determined by measuring protophyrin IX fluorescence as described above.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An apparatus for delivering a compound through an epithelial tissue layer, the apparatus comprising a reservoir for containing a coupling medium suitable for mixing with the compound, wherein the reservoir is arranged to enable the coupling medium to directly contact a surface of the epithelial tissue layer;

an energy source; and a target material arranged between the energy source and the reservoir, wherein the reservoir is configured to enable the target material to directly contact coupling medium in the reservoir, and the energy source and the target material are arranged, and the energy source is controlled, so that energy from the energy source directed onto the target material propagates an impulse transient within the coupling medium.

2. An apparatus of claim 1, wherein the energy source is a laser.

3. An apparatus of claim 2, further comprising a transparent material bonded to a surface of the target material and interposed between the surface and the laser, and arranged to confine pressure forces resulting from ablation of the target material within the reservoir.

4. An apparatus of claim 2, wherein the target material comprises a polymer.

5. An apparatus of claim 1, wherein the target material is a metal foil or plastic sheet.

6. An apparatus of claim 5, wherein the metal foil comprises aluminum or copper.

7. The apparatus of claim 1, wherein the energy source propagates impulse transients that each comprise a broadband compressive wave having a rise time of at least 1 nanosecond and a peak pressure of at least 300 bar and no more than 2000 bar.

8. The apparatus of claim 7, wherein the impulse transients have a peak pressure of 550 to 650 bar.

9. The apparatus of claim 7, wherein the impulse transients have a rise time of 75 to 125 nanoseconds.

10. The apparatus of claim 1, wherein the energy source is a pulsed laser beam.

11. A system for delivering a compound through an epithelial cell layer in an animal, the system comprising an apparatus of claim 1; and a coupling medium suitable for mixing with the compound.

12. The system of claim 11, wherein the coupling medium comprises a non-linear liquid or gel.

13. The system of claim 11, wherein the coupling medium comprises water, oil, an isotonic medium, a collagenous gel, or any combination thereof.

14. The system of claim 11, wherein the coupling medium comprises a surfactant.

15. The system of claim 11, wherein the energy source propagates impulse transients that each comprise a broadband compressive wave having a rise time of at least 1 nanosecond and a peak pressure of at least 300 bar and no more than 2000 bar.

16. The system of claim 15, wherein the impulse transients have a peak pressure of 550 to 650 bar.

17. The system of claim 15, wherein the impulse transients have a rise time of 75 to 125 nanoseconds.

18. The system of claim 15, wherein the energy source is a pulsed laser beam.

* * * * *

UNITED STATES PATENT AND TRADEMARK OFFICE
CERTIFICATE OF CORRECTION

PATENT NO. : 6,689,094 B2
DATED : February 10, 2004
INVENTOR(S) : Kollias et al.

It is certified that error appears in the above-identified patent and that said Letters Patent is hereby corrected as shown below:

Title page,
Item [*] Notice, delete "by 36 days" and insert -- by 0 days --

Signed and Sealed this

Fifteenth Day of February, 2005

JON W. DUDAS
*Director of the United States Patent and Trademark Office*